United States Patent [19]

Alvarez

[11] 4,177,811
[45] Dec. 11, 1979

[54] THERAPEUTIC APPLICATOR AND CLEANSING DEVICE

[76] Inventor: Marcial Alvarez, 225 E. Jersey St., Elizabeth, N.J. 07206

[21] Appl. No.: 833,070

[22] Filed: Sep. 14, 1977

Related U.S. Application Data

[63] Continuation-in-part of Ser. No. 744,403, Nov. 23, 1976, abandoned.

[51] Int. Cl.² ........................ A61M 35/00; B08B 1/00
[52] U.S. Cl. .................................. 128/261; 15/104.93
[58] Field of Search ............... 128/254, 261, 265, 255, 128/403, 260, 401, 269, 267, 341, 342, 271, 283; 224/26 J; 225/1, 94; 229/51 C, 87 C; 424/14–18; 401/28, 36, 37, 192, 292; 15/104.94, 104.93

[56] References Cited

U.S. PATENT DOCUMENTS

| | | | |
|---|---|---|---|
| 1,610,947 | 12/1926 | Hosmer | 128/254 |
| 2,333,342 | 5/1942 | Slocumb | 128/271 |
| 2,554,137 | 5/1951 | Burton | 229/87 C |
| 2,779,465 | 1/1957 | Anderson | 206/47 |

FOREIGN PATENT DOCUMENTS

| | | | |
|---|---|---|---|
| 379146 | 10/1907 | France | 128/271 |
| 519197 | 3/1940 | United Kingdom | 128/261 |

*Primary Examiner*—Dalton L. Truluck
*Assistant Examiner*—Thomas Wallen

*Attorney, Agent, or Firm*—Weingram & Klauber

[57] ABSTRACT

A cleansing and applicator device is disclosed, which is especially useful in treatment of the perineal area of the human anatomy. The device comprises a generally conically shaped applicator body, formed preferably of a good heat conductor, the device being hollow and closed at the base thereof by a removable cap, whereby a cooling or heating liquid may be provided to the body interior. A flexible and compressible covering structure for effecting cleansing and treatment is fitted about and thereby encloses at least the portion of the applicator body including the apex. The covering structure preferably includes multiple layers, including at least one moisture-absorbent layer. The applicator body may include a necked-in portion toward the base thereof, so that the covering structure can be frictionally secured to the body, such as with an elastic band or a clamp. The plural layers comprising the covering structure, preferably include tear lines, which enables the various layers to be successively separated from the applicator device for disposal. The covering structure may include an outermost liquid-impervious protective layer as for example, of plastic, cellophane or the like; with an absorbent layer. Beneath the absorbent layer, a further liquid-impervious protective layer may be provided, and beneath this a layer of paper or the like which is impregnated with a soothing medication such as an oil or the like.

13 Claims, 3 Drawing Figures

U.S. Patent    Dec. 11, 1979    4,177,811
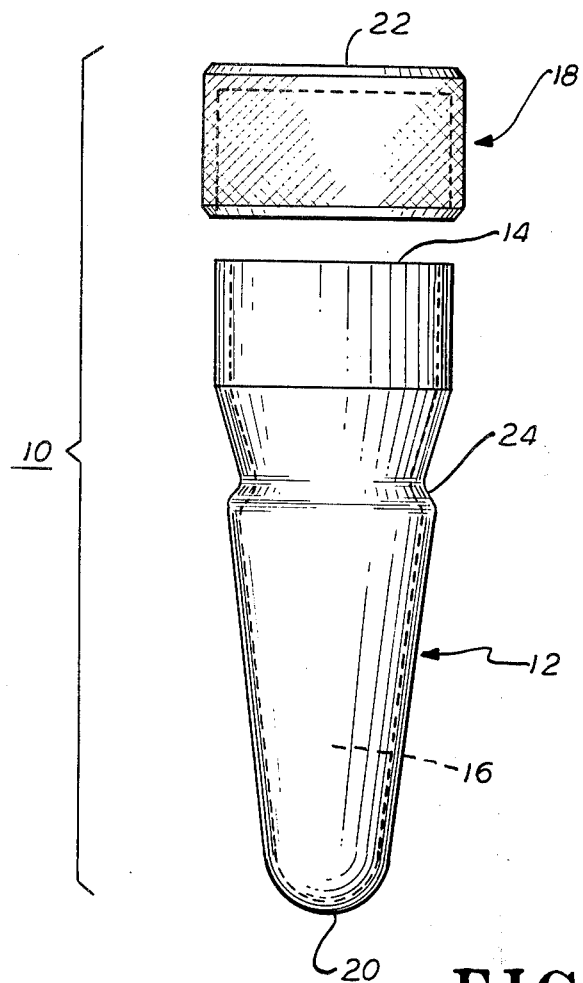
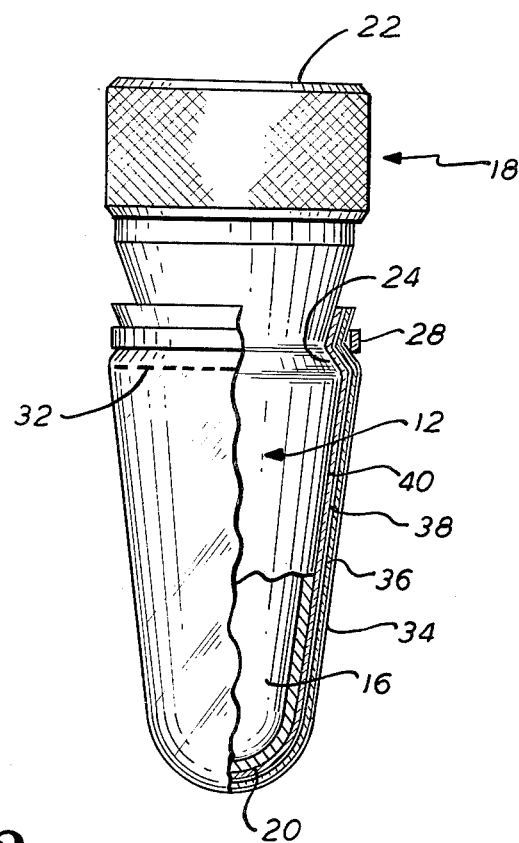
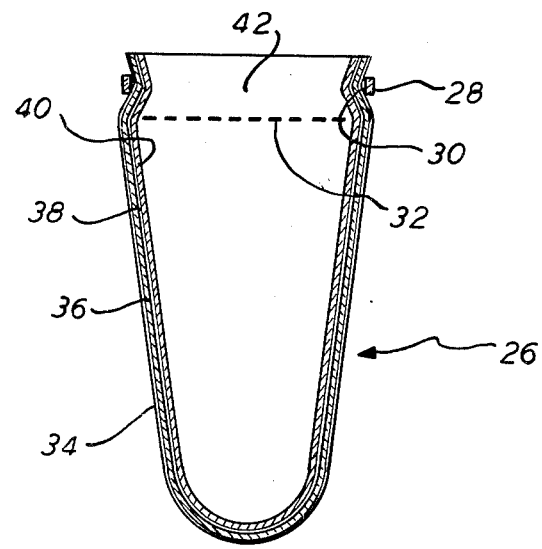

THERAPEUTIC APPLICATOR AND CLEANSING DEVICE

BACKGROUND OF INVENTION

This application is a continuation-in-part of my co-pending application; Ser. No. 744,403, filed Nov. 23, 1976, for "Perineal Toilet Cone," abandoned.

This invention relates generally to medical apparatus, and more specifically relates to devices useful in the cleansing and treatment of the perineal portion of the human anatomy, and useful as well in treatment of hemorrhoids.

As one aspect of personal hygiene, individuals are often required to effect cleansing of the perineal area of the anatomy, for example, subsequent to defecation. Particularly, where pathological conditions are present, including irritation of the anal and/or perineal areas and/or the presence of hemorrhoids, it is important that such cleansing be effected thoroughly, under reasonably sanitary, i.e., hygienic conditions; and further, it may be important where irritations or the like are present, to provide soothing medications or the like to the afflicted area.

In the past, individuals faced with the aforementioned problems have found it extremely difficult to effect a suitable solution. It will, for example, be evident that such individuals may require the above-mentioned treatment while away from home or other facilities where medical resources are readily available. Under such circumstances, the individual is often simply unable to provide the appropriate medical treatment, and a resulting aggravation of a condition can ensue.

In accordance with the foregoing, it may be regarded as an object of the present invention, to provide a therapeutic device which is portable and conveniently carried by a user thereof, which device is useful in the cleansing of the perineal portions of the anatomy.

It is a further object of the present invention to provide a device of the aforementioned character, which enables hygienic cleansing and treatment of the perineal portions of the anatomy, without requiring the user to contact the said areas with the fingers, thereby avoiding irritation of the area by the fingers or nails, and also avoiding the possible consequences of unsanitary contact.

It is a further object of the present invention, to provide a device of the aforementioned character, which is useful in the treatment of hemorrhoids, and especially in treatment of hemorrhoids to effect reduction thereof.

It is a further object of the invention, to provide a device as aforementioned, which includes means enabling the device to be readily heated or cooled, to thereby facilitate treatment of hemorrhoids or other pathological conditions.

SUMMARY OF THE INVENTION

Now in accordance with the present invention, the foregoing objects, and others, as will become apparent in the course of the ensuing specification, are achieved in a cleansing and applicator device, which is especially useful in treatment of the perineal area of the human anatomy.

The device comprises a generally conically shaped applicator body, formed preferably of aluminum or other good heat conductor, the device being hollow and closed at the base thereof by a removable cap. A flexible and compressible covering structure for effecting cleansing and treatment is fitted about and thereby encloses at least the portion of the applicator body including the apex. The covering structure preferably includes multiple layers, including at least one moisture-absorbent layer, as for example, of paper, fabric or the like. The applicator body may include a necked-in portion toward the base thereof, so that the covering structure can be frictionally secured to the body by elastic retaining means, such as an elastic band or a C clamp or the like, which passes about the covering structure to compress same against the necked-in portion of the applicator body. The plural layers comprising the covering structure, preferably include tear lines, which reside toward the apex side of the necked-in body portion. This enables the various layers to be successively separated from the applicator device for disposal.

The covering structure may include an outermost liquid-impervious protective layer as for example, of plastic, cellophane or the like; with an absorbent layer, e.g., of paper underlying the protective layer. Beneath the said absorbent layer, a further liquid-impervious protective layer may be provided and beneath this a layer of paper or the like which is impregnated with a soothing medication such as an oil or the like.

The aforementioned structure may be employed by the user detaching and removing the outermost protective cover, and thereupon making use in cleansing of the underlying absorbent layer. Upon detaching the latter (and the successive second protective layer), the oil-impregnated layer becomes accessible, which layer may be utilized for treating the afflicted perineal area, i.e., by applying the soothing oil composition to the said area. The said impregnated layer may, of course, also include various other compositions known to be useful in treatment of the irritated portion of the anatomy.

The covering structure can also comprise other combinations of layers. For example, a series of medication-impregnated layers separated by liquid-impervious layers can be provided; or a series of absorbent layers either separated or not by protective liquid-impervious layers, can be provided.

The said applicator body, with the covering structure removed, is per se useful in the treatment of hemorrhoids or the like. The structure as it is hollow, may thus be provided with a cooling or heating liquid; and the smooth apex portion may be manually inserted into the anal sphincter to effect reduction of hemorrhoids or so forth.

BRIEF DESCRIPTION OF DRAWINGS

The invention is diagrammatically illustrated, by way of example, in the drawing appended hereto in which:

FIG. 1 is an exploded side elevational view, of an applicator body in accordance with the present invention; and FIG. 2 is a longitudinal, cross-sectional view, of a covering structure utilizable with the device of FIG. 1;

FIG. 3 is a side elevational view, partially broken away and sectioned, depicting the covering structure and applicator body in associative relationship.

DESCRIPTION OF PREFERRED EMBODIMENT

In FIG. 1 herein, an exploded, side elevational view appears of an applicator body 10 in accordance with the present invention. Body 10 is shown in FIG. 1 separate from the covering structure with which it may in one aspect thereof be used. Applicator body 10 is seen to include a main portion 12 which comprises a hollow, generally tapering body which is open at end 14 thereof, to enable access to the interior 16 for filling same with a liquid or the like, as may be desired. A removable cap 18 is provided, which interfits with and closes the open end 14 of portion 12. The said cap is fitted upon portion 12 by a simple pressure fit, which yet provides a fluid-tight seal. Cap 18 may also be secured to portion 12 by other means known in the art, including threading thereupon. Other materials than the aluminum mentioned may be used for both the portion 12 and cap 18. For reasons as will be discussed below, it is advantageous, however, for the material comprising especially portion 12 to be a relatively good heat conductor; and it is also significant for the outer surface of portion 12, including especially the apex portion 20 to be relatively smooth.

It is thus seen that with cap 18 placed upon portion 12, the resulting applicator body 10 can be regarded as of generally cone-like or (in some instances) paraboloidal shape, i.e., the shape of the said body tapers from a relatively flat base 22 to a smoothly rounded apex 20, with however, a necked-in portion 24 being provided intermediate base 14 and apex 20.

As thus far described, the present device can be used without further structure, particularly in the treatment of hemorrhoids or similar afflictions at the anal tract. Thus, for these purposes, it is quite suitable for the cap 18 to be removed and a cooling or heating composition provided within the interior 16 of body 10. For example, an ice-water mixture may be thus provided, or a heated liquid. Under these circumstances, the individual using body 10 can insert the apex portion 20 into the anus to effect treatment of hemorrhoids, and thereby reduction of same.

It may also be noted in the foregoing connection, that the hollow interior 16 of body 10 can serve an additional purpose, i.e., various medicaments in small packages or the like can be carried within the interior of the device. This enables the said device, which itself is readily portable, to be used as a convenient carrier for the medicaments or treating compositions which may be used in connection with employment of the device, or which may be separately used.

In FIG. 2, a diagrammatic cross-section is set forth of a covering structure 26 utilizable with the applicator body 10. It will be seen that the basic cross-sectional form of structure 26 is geometrically similar to that of body 10. In consequence, it will be evident that covering structure 26 fits directly about portion 12 of body 10, i.e., conversely one can say that portion 12 nests directly within structure 26. When the association is thus made, a clamping means 28 passes about the necked-in portion 30 of structure 26. The said clamping means is preferably elastic, and can, e.g., be a simple elastic band or an elastically expandable U or C clamp, or the like. Fastener 28 maintains the covering structure 26 in its associative relationship with applicator body 10. The user may purchase a plurality of the covering structures 26, i.e., such structures can be commercially sold in packages of nested units, and the user associates one of the said structures (as in FIG. 3) with the body 10 prior to use of the present device.

Referring to FIG. 2 and also to the view of FIG. 3 showing covering structure 26 operatively associated with body 10, it is seen that structure 26 is characterized by a plurality of overlying layers of flexible, compressible material. Each of these layers is preferably provided with a tear line 32, i.e., a perforated, scored or weakened line, the function of which is to enable the user to tear away, and thereby remove the successive layers upon use of the present device. Line 32 can also comprise a separable "tear strip," i.e., of the type used, e.g., in cigarette packages or the like—this latter type of structure being advantageous in avoiding unnecessary finger contact with the layers of structure 26.

The outer layer 34 of structure 26 preferably comprises a simple protective layer, which is liquid-impervious and non-absorbent. This layer may thus comprise cellophane or a thin plastic, such as polyethylene or polyvinyl chloride, or so forth—all such materials being well-known for protective packaging.

Beneath layer 34, which is torn away by the user prior to employing the present device, is an absorbent layer 36, preferably of soft fibrous paper. The said layer may also comprise other absorbent materials such as fabric or the like. Layer 36 serves in use of the present device, to effect cleansing of the perineal area, i.e., the user having torn away the outer protective layer 34, now proceeds—handling the present device by the base—to pat or dab the portions of the anatomy to be cleansed. Following this procedure, the said absorbent layer is detached as aforementioned, and discarded.

Beneath absorbent layer 36, is a further protective layer 38, again of a liquid-impervious material, such as the aforementioned cellophane, plastic or the like. This layer is now torn away, and in turn, exposes an underlying layer 40, which in this instance is of paper, fabric or the like, and is preferably impregnated with a soothing composition having medicinal properties, as, for example, a mineral oil or the like. In operation, the user of the device having now torn away the second protective layer 38, exposes the impregnated layer 40, which may then be used to apply the soothing medicament to the perineal area.

Once the entire covering structure 26 is so used, the remaining portions of the structure, i.e., the upper part 42, can be detached by loosening or expanding the clamping means 28, and a further, replacement structure provided and affixed to the device.

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed and limited only by the scope and spirit of the claims now appended hereto.

I claim:

1. A cleansing and applicator device for treatment of the perineal area of the human anatomy, comprising in combination:

a generally conically shaped applicator body, said body generally tapering from the base to the apex thereof;

a flexible and compressible covering structure for effecting said cleansing being fitted about and thereby enclosing at least the portion of the said body including said apex; said structure being a composite of overlying layers of material, at least one said layer being moisture-absorbent and another said layer being liquid impervious, the layers of said composite being readily detachable from said structure and thereby from said applicator body by a user of said device to effect disposal of said layers after use thereof; and means removably securing said covering structure to said applicator body, whereby said covering structure may be replaced following use of the layers thereof.

2. A device in accordance with claim 1, wherein said applicator body includes a necked-in portion towards the base thereof; and wherein said covering structure extends to cover said necked-in portion and is secured to said body by clamping means passing about said structure at said necked-in portion and compressing said structure against said necked-in portion.

3. A device in accordance with claim 2, wherein at least some of said layers comprising said covering structure include weakened portions passing circumferentially about the layers toward the apex-facing side of said necked-in portion, whereby layers of said structure so provided may be selectively detached for disposal.

4. A device in accordance with claim 3, wherein said covering structure includes at least an outermost fluid-impervious protective layer, and an absorbent layer underlying said protective layer for effecting cleansing of said perineal area.

5. A device in accordance with claim 4, wherein said absorbent layer comprises paper.

6. A device in accordance with claim 4, wherein said covering structure further includes a second liquid-impervious protective layer underlying said absorbent layer, and wherein a medication-impregnated layer underlies said second protective layer for treating said cleansed perineal area upon detachment of the layer overlying said impregnated layer.

7. A device in accordance with claim 6, wherein each of said layers includes said weakened portions to enable successive exposure thereof.

8. A device in accordance with claim 1, wherein said applicator body is hollow and includes a removable cap member closing the base thereof, whereby the interior of said body is accessible for provision therein of heating or cooling liquids.

9. A device in accordance with claim 8, wherein said applicator body comprises a metal; and where at least the apex and adjacent portions are provided with a smooth surface to enable the use of said device with said covering structure removed for direct insertion at the anal area of the anatomy for treatment of anal disorders.

10. A cleansing and applictor device for treatment of the perineal area of the human anatomy, comprising in combination:

an elongated applicator body, tapering from the base thereof to a relatively rounded apex portion; and a flexible and compressible covering structure for effecting said cleansing and application, said structure being removably nested about and thereby enclosing at least the portions of said applicator body including said apex; said structure being a composite including a plurality of overlying layers, at least one said layer being moisture-absorbent and another said layer being liquid-impervious, said layers being successively detachable from said structure and thereby from said body by a user of said device to effect disposal thereof; and means removably securing said covering structure to said applicator body, whereby said structure may be replaced following use of said layers.

11. A device in accordance with claim 10, wherein at least some of said layers comprising said covering structure include structurally weakened lines passing about the layers toward the base of said applicator body, whereby said layers may be selectively detached for disposal by separating at said lines.

12. A device in accordance with claim 11, wherein said covering structure is frictionally secured to said applicator body by clamping means passing about said structure and said body.

13. A device in accordance with claim 12, wherein said tear lines are situated to the apex-facing side of said clamping means, whereby said layers may be removed from said covering structure by separation at said lines with the remainder of said structure remaining clamped to said body.

* * * * *